(12) United States Patent
Lee

(10) Patent No.: US 8,835,521 B2
(45) Date of Patent: Sep. 16, 2014

(54) PHOTOSENSITIVE COMPOSITION AND COMPOUND FOR USE IN THE PHOTOSENSITIVE COMPOSITION

(75) Inventor: Keon Woo Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 57 days.

(21) Appl. No.: 13/549,753

(22) Filed: Jul. 16, 2012

(65) Prior Publication Data

US 2013/0029271 A1   Jan. 31, 2013

(30) Foreign Application Priority Data

Jul. 15, 2011  (KR) ........................ 10-2011-0070644
May 29, 2012  (KR) ........................ 10-2012-0056628

(51) Int. Cl.
| | | |
|---|---|---|
| *C08F 2/50* | (2006.01) | |
| *C07F 7/00* | (2006.01) | |
| *G03F 7/027* | (2006.01) | |
| *G03F 7/075* | (2006.01) | |
| *G03F 7/00* | (2006.01) | |

(52) U.S. Cl.
CPC . *G03F 7/075* (2013.01); *C07F 7/00* (2013.01); *G03F 7/027* (2013.01); *G03F 7/0755* (2013.01); *G03F 7/0007* (2013.01)
USPC .............................. 522/6; 526/323; 526/323.2

(58) Field of Classification Search
CPC ......... C08K 5/5419; C07F 7/18; G03F 7/075; G03F 7/033

USPC .................................... 522/6; 526/323, 323.2
See application file for complete search history.

(56) References Cited

U.S. PATENT DOCUMENTS

| 4,927,949 | A | | 5/1990 | Kabeta et al. | |
|---|---|---|---|---|---|
| 5,464,900 | A | * | 11/1995 | Stofko et al. | ................. 524/838 |
| 2009/0208854 | A1 | | 8/2009 | Choi et al. | |

FOREIGN PATENT DOCUMENTS

| JP | 2-96583 A | 4/1990 |
|---|---|---|
| JP | 08-269071 A | 10/1994 |
| KR | 10-0655047 B1 | 11/2006 |
| TW | 200823576 A1 | 6/2008 |

OTHER PUBLICATIONS

Office Action and English Translation issued in corresponding Taiwanese Patent Application No. 101120870, on Feb. 7, 2014, 11 pages.
International Search Report issued in International Application No. PCT/KR2012/004465 on Jan. 2, 2013, 2 pages.
Written Opinion issued in International Application No. PCT/KR2012/004465 on Jan. 2, 2013 along with English translation, 10 pages.

* cited by examiner

*Primary Examiner* — Kuo-Liang Peng
(74) *Attorney, Agent, or Firm* — Rothwell, Figg, Ernst & Manbeck, P.C.

(57) ABSTRACT

Disclosed are a photosensitive composition and a compound used in the same. If the composition provided through the present application is used, it is possible to form a thin film having improved adhesion strength of a pattern.

18 Claims, No Drawings

PHOTOSENSITIVE COMPOSITION AND COMPOUND FOR USE IN THE PHOTOSENSITIVE COMPOSITION

CROSS-REFERENCE TO RELATED APPLICATIONS

This application claims priority to and the benefit of Korean Patent Application Nos. 10-2011-0070644 and 10-2012-0056628 filed in the Korean Intellectual Property Office on Jul. 15, 2011 and May 29, 2012, respectively, the entire contents of which are incorporated herein by reference.

TECHNICAL FIELD

The present application relates to a photosensitive composition and a compound for use in the photosensitive composition.

BACKGROUND ART

Various photosensitive materials are used to manufacture a color filter of a liquid crystal display diode. For example, a pigment-dispersed photosensitive material may be used in order to form a color pixel. In addition, a black matrix that is a black partition acting as a light-blocking film blocking light may be manufactured by using a solution where a black pigment, carbon black, perylene black, titanium dioxide or the like is dispersed in a photosensitive material. An overcoat for correcting a step between pixels and a column spacer for maintaining a cell gap of a liquid crystal display diode may be manufactured by using a transparent photosensitive material including no pigment. Further, a photosensitive composition used while the column spacer or the overcoat is manufactured may be used as a passivation of a thin film transistor layer. If the photosensitive material is applied on a glass substrate or a glass substrate coated with indium tin oxides and then processed through a photolithography process, a color filter single substrate is achieved.

If resolution of the liquid crystal display diode is improved in order to implement a higher level of image, resolution of the color filter is increased. The sizes of the pixel, the black matrix, the column spacer and the like are reduced in order to manufacture the color filter having high resolution. In this case, attachment strength between the thin film of the photosensitive material and the lower substrate during the process becomes poor, thus increasing a possibility of occurrence of defects due to losing a portion of the pattern. There is a demand for increasing attachment strength between the photosensitive material and the lower substrate as compared to the related art.

SUMMARY OF THE INVENTION

The present application has been made in an effort to provide a photosensitive composition and a novel compound used in the photosensitive composition.

An exemplary embodiment of the present application provides a photosensitive composition including: a coupling agent including one or more of compounds represented by the following Formula 1; a binder resin including an alkali soluble polymer resin; a crosslinking compound including two or more ethylenically unsaturated groups; a photopolymerization initiator; and a solvent:

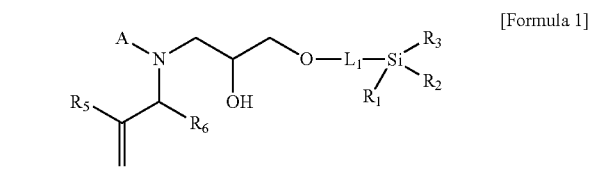

wherein
$L_1$ is hydrogen or a $C_3$-$C_8$ alkylene group substituted or unsubstituted by a $C_1$-$C_6$ alkyl group,
$R_1$ to $R_3$ are each independently a $C_1$-$C_3$ alkoxy group,
A is a $C_1$ to $C_3$ alkyl group or a $C_2$-$C_{14}$ alkenyl group,
$R_5$ is hydrogen or a $C_1$-$C_3$ alkyl group, and
$R_6$ is hydrogen or a $C_1$-$C_8$ alkyl group.

Another exemplary embodiment of the present application provides a photosensitive material manufactured by using the photosensitive composition.

Yet another exemplary embodiment of the present application provides a compound represented by the following Formula 2.

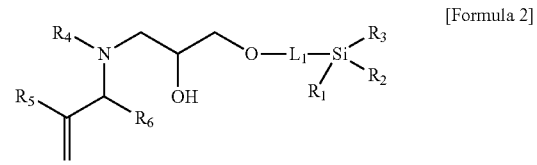

wherein $L_1$ is hydrogen or a $C_3$-$C_8$ alkylene group substituted or unsubstituted by a $C_1$-$C_6$ alkyl group, $R_1$ to $R_3$ are each independently a $C_1$-$C_3$ alkoxy group, $R_4$ is a $C_1$-$C_3$ alkyl group, $R_5$ is hydrogen or a $C_1$-$C_3$ alkyl group, and $R_6$ is hydrogen or a $C_1$-$C_8$ alkyl group.

Yet another exemplary embodiment of the present application provides a compound represented by the following Formula 3.

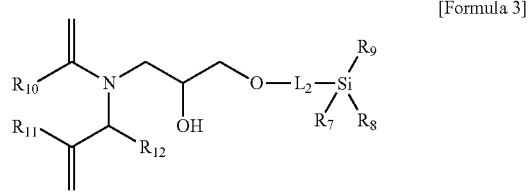

wherein $L_2$ is hydrogen or a $C_3$-$C_8$ alkylene group substituted or unsubstituted by a $C_1$-$C_6$ alkyl group, $R_7$ to $R_9$ are each independently a $C_1$-$C_2$ alkoxy group, $R_{12}$ and $R_{11}$ are each independently hydrogen or a $C_1$-$C_2$ alkyl group, and $R_{12}$ is hydrogen or a $C_1$-$C_8$ alkyl group.

According to the exemplary embodiments of the present application, since the photosensitive composition using the compound provided through the present application has an effect that there is a small possibility of losing a thin film during a developing process, it is possible to form the thin film having improved adhesion strength of a pattern.

DETAILED DESCRIPTION

Hereinafter, the present application will be described in more detail.

An exemplary embodiment of the present application provides a photosensitive composition including a coupling agent including one or more of compounds represented by Formula 1; a binder resin including an alkali soluble polymer resin; a crosslinking compound including two or more ethylenically unsaturated groups; a photopolymerization initiator; and a solvent.

The exemplary embodiment of the present application provides a compound represented by Formula 2 or Formula 3. The compound represented by Formula 2 or Formula 3 may be a compound to be used in the photosensitive composition.

The compound represented by Formula 1 according to the exemplary embodiment of the present application may be a compound represented by the following Formula 2.

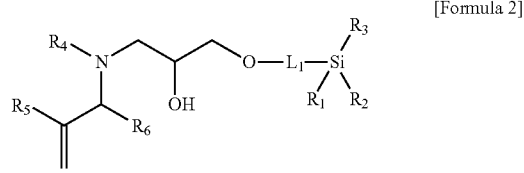

[Formula 2]

wherein
$L_1$ is hydrogen or a $C_3$-$C_8$ alkylene group substituted or unsubstituted by a $C_1$-$C_6$ alkyl group,
$R_1$ to $R_3$ are each independently a $C_1$-$C_3$ alkoxy group,
$R_4$ is a $C_1$-$C_3$ alkyl group,
$R_5$ is hydrogen or a $C_1$-$C_3$ alkyl group, and
$R_6$ is hydrogen or a $C_1$-$C_8$ alkyl group.

The compound represented by Formula 1 according to the exemplary embodiment of the present application may be a compound represented by the following Formula 3.

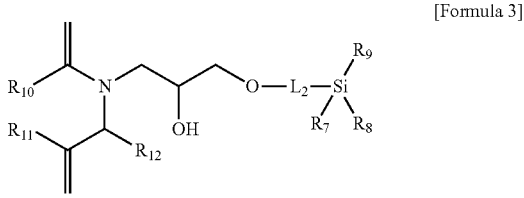

[Formula 3]

wherein
$L_2$ is hydrogen or a $C_3$-$C_8$ alkylene group substituted or unsubstituted by a $C_1$-$C_6$ alkyl group,
$R_7$ to $R_9$ are each independently a $C_1$-$C_3$ alkoxy group,
$R_{10}$ and $R_{11}$ are each independently hydrogen or a $C_1$-$C_3$ alkyl group, and
$R_{12}$ is hydrogen or a $C_1$-$C_8$ alkyl group.

The compound represented by Formula 1 according to the exemplary embodiment of the present application may be a compound represented by the following Formula 4.

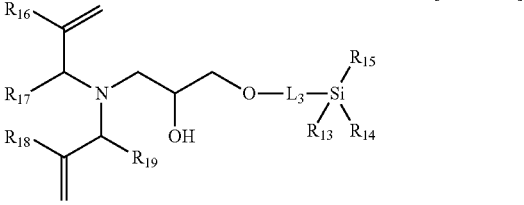

[Formula 4]

wherein
$L_3$ is hydrogen or a $C_3$-$C_8$ alkylene group substituted or unsubstituted by a $C_1$-$C_6$ alkyl group,
$R_{13}$ to $R_{15}$ are each independently a $C_1$-$C_3$ alkoxy group,
$R_{16}$ and $R_{18}$ are each independently hydrogen or a $C_1$-$C_3$ alkyl group, and
$R_{17}$ and $R_{19}$ are each independently hydrogen or a $C_1$-$C_8$ alkyl group.

The compound represented by Formula 1 includes tertiary amine and a C=C double bond together with a siloxane group.

In the compound according to the exemplary embodiment of the present application, substituent groups of Formula 1, Formula 2, Formula 3 and Formula 4 will be described in more detail below.

The alkylene group included in $L_1$ to $L_3$ may be a straight chain or a branched chain, and the number of carbon atoms may be 3 to 8. The alkylene group may be substituted or unsubstituted by hydrogen or a $C_1$-$C_6$ alkyl group. Specific examples of the alkylene group include methylene, ethylene, propylene, isopropylene, butylene, t-butylene and the like, but are not limited thereto.

$R_4$, $R_5$, $R_{10}$, $R_{11}$, $R_{16}$ and $R_{18}$ may be a $C_1$-$C_3$ alkyl group. These may be a straight chain or a branched chain. Specific examples of the alkyl group include a methyl group, an ethyl group, a propyl group, an isopropyl group, a butyl group, a t-butyl group and the like, but are not limited thereto.

$R_6$, $R_{12}$, $R_{17}$ and $R_{19}$ may be a $C_1$-$C_8$ alkyl group. These may be a straight chain or a branched chain. Specific examples of the alkyl group include a methyl group, an ethyl group, a propyl group, an isopropyl group, a butyl group, a t-butyl group and the like, but are not limited thereto.

$R_1$ to $R_3$, $R_7$ to $R_9$ and $R_{13}$ to $R_{15}$ may be an alkoxy group. These may be a straight chain or a branched chain and a substituted or unsubstituted matter, and the number of carbon atoms may be 1 to 3. Examples of the alkoxy group may include a methoxy group, an ethoxy group, an isopropyloxy group and the like, but are not limited thereto.

The term "substituted or unsubstituted" means that something is substituted by one or more substituent groups or there is no substituent group.

In the compound according to the exemplary embodiment of the present application, specific examples of the compound represented by Formula 2 are as follows, but are not limited thereto.

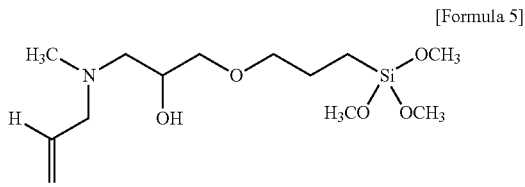 [SMILES: C=CCN(C)CC(O)COCCC[Si](OC)(OC)OC]

[Formula 5]

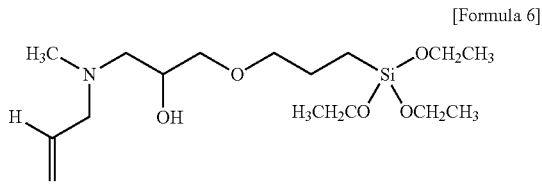

[Formula 6]

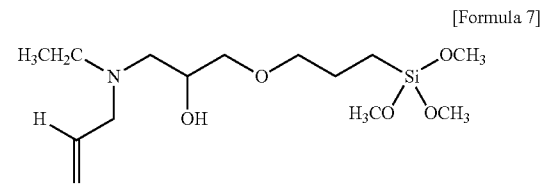

[Formula 7]

[Formula 8]

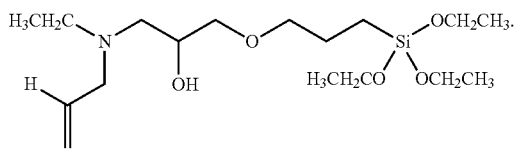

Specific examples of the compound represented by Formula 4 are as follows, but are not limited thereto.

[Formula 9]

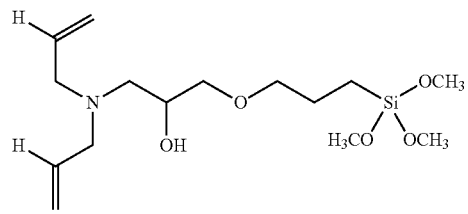

[Formula 10]

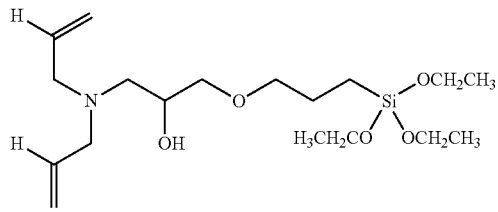

In the photosensitive composition according to the exemplary embodiment of the present application, the coupling agent including one or more of the compounds represented by Formula 1 may be included in the amount of 0.01 to 1.32 wt % based on the total weight of the photosensitive composition. In the case where the coupling agent is included in the amount of 0.01 wt % or more, an effect by the coupling agent is excellent, and in the case where the coupling agent is included in the amount of 1.32 wt % or less, there may be an advantage in view of storage stability of products.

In the photosensitive composition according to the exemplary embodiment of the present application, the content of the coupling agent including one or more of the compounds represented by Formula 1, Formula 2, Formula 3 and Formula 4 may be 0.05 to 5 wt % based on the total weight of the solid. In the case where the coupling agent is included in the amount of 0.05 wt % or more, an effect by the coupling agent is excellent, and in the case where the coupling agent is included in the amount of 5 wt % or less, there may be an advantage in view of storage stability of products.

Since the photosensitive composition according to the exemplary embodiment of the present application includes the binder resin, there is an effect of controlling viscosity and there is an effect that patterning using an alkali developing solution is feasible. Matters, such as an alkali soluble polymer resin, which are generally used in the art may be used as the binder. Specifically, an acryl-based binder resin including a carboxyl group may be used as the alkali soluble matter, and, preferably, a matter having a weight average molecular weight of 3,000 to 150,000 is used.

In the photosensitive composition according to the exemplary embodiment of the present application, the content of the binder resin may be 1 to 20 wt % based on the total weight of the photosensitive composition, but is not limited thereto. If the content of the binder resin is 1 wt % or more, there is an effect in which the pattern is performed well by using the alkali aqueous solution, if the content is 20 wt % or less, there is an effect of preventing the pattern from being lost during the developing process.

In the photosensitive composition according to the exemplary embodiment of the present application, specifically, a crosslinking compound including an ethylenically unsaturated group may be used as the crosslinking compound. To be more specific, a crosslinking compound including two or more unsaturated acryl groups or a crosslinking compound including three or more unsaturated acryl groups may be used. Specific examples of the crosslinking compound may include one or more kinds selected from the group consisting of a compound that is obtained by esterifying polyvalent alcohol such as ethyleneglycol di(metha)acrylate, polyethylene glycol di(metha)acrylate in which the number of ethylene groups is to 14, trimethylolpropane di(metha)acrylate, trimethylolpropane tri(metha)acrylate, pentaerythritol tri(metha)acrylate, pentaerythritol tetra(metha)acrylate, 2-trisacryloyloxymethylethyl phthalate, propylene glycol di(metha)acrylate in which the number of propylene groups is 2 to 14, dipentaerythritol penta(metha)acrylate, dipentaerythritol hexa(metha)acrylate, and a mixture of an acidic denatured material of dipentaerythritol penta(metha)acrylate and dipentaerythritol hexa(metha)acrylate (trademark: TO-2348, and TO-2349 manufactured by Toagosei, Co., Ltd. in Japan) by a $\alpha,\beta$-unsaturated carboxylic acid; a compound that is obtained by adding a (metha)acrylic acid to a compound including a glycidyl group such as an addition product of trimethylolpropane triglycidyletheracrylic acid and an addition product of bisphenol A diglycidyletheracrylic acid; an addition product of a hydroxyl group such as diester phthalate of $\beta$-hydroxyethyl(metha)acrylate and an addition product of toluene diisocyanate of $\beta$-hydroxyethyl (metha)acrylate, or an addition product of a compound having an ethylene unsaturated bond and an ester compound with polyvalent carboxylic acid or polyisocyanate; (metha)acrylate alkylester such as methyl (metha)acrylate, ethyl(metha)acrylate, butyl(metha)acrylate, and 2-ethylhexyl(metha)acrylate; and 9,9'-bis[4-(2-acryloyloxyethoxy)phenyl]fluorine, but are not limited thereto, and general matters that are known in the art may be used. In some cases, a silica dispersing agent may be used in these compounds, and examples thereof include Nanocryl XP series (0596, 1045, 21/1364) and Nanopox XP series(0516, 0525) manufactured by Hanse Chemie, Co., Ltd.

In the photosensitive composition according to the exemplary embodiment of the present application, the content of the crosslinking compound may be 1 to 30 wt % based on the total weight of the photosensitive composition, but is not limited thereto.

In the photosensitive composition according to the exemplary embodiment of the present application, as the photopolymerization initiator, for example, a triazine-based compound such as 2,4-trichloromethyl-(4'-methoxyphenyl)-6-triazine, 2,4-trichloromethyl-(4'-methoxystyryl)-6-triazine, 2,4-trichloromethyl-(fipronil)-6-triazine, 2,4-trichloromethyl-(3',4'-dimethoxyphenyl)-6-triazine, 3-{4-[2,4-bis (trichloromethyl)-s-triazine-6-yl]phenylthi} propanoic acid, 2,4-trichloromethyl-(4'-ethylbiphenyl)-6-triazine, and 2,4-trichloromethyl-(4'-methylbiphenyl)-6-triazine; a biimidazole compound such as 2,2'-bis(2-chlorophenyl)-4,4',5,5'-tetraphenyl biimidazole, and 2,2'-bis(2,3-dichlorophenyl)-4,4', 5,5'-tetraphenylbiimidazole; an acetophenone-based compound such as 2-hydroxy-2-methyl-1-phenylpropane-1-one, 1-(4-isopropylphenyl)-2-hydroxy-2-methylpropane-1- one, 4-(2-hydroxyethoxy)-phenyl (2-hydroxy)propyl ketone, 1-hydroxycyclohexyl phenyl ketone, 2,2-dimethoxy-2-phenyl acetophenone, 2-methyl-(4-methylthiophenyl)-2-morpholino-1-propane-1-one(Irgacure-907), and 2-benzyl-2-dimethylamino-1-(4-morpholinophenyl)-butane-1-one (Irgacure-369); an O-acyloxime-based compound such as Irgacure OXE 01 and Irgacure OXE 02 manufactured by Ciba Geigy, Co., Ltd.; a benzophenone-based compound such as 4,4'-bis(dimethylamino)benzophenone, and 4,4'-bis(diethylamino)benzophenone; a thioxantone-based compound such as 2,4-diethyl thioxantone, 2-chloro thioxantone, isopropyl thioxantone, diisopropyl thioxantone; a phosphine oxide-based compound such as 2,4,6-trimethylbenzoyl diphenylphosphine oxide, bis(2,6-dimethoxybenzoyl)-2,4,4-trimethylpentyl phosphine oxide, and bis(2,6-dichlorobenzoyl) propyl phosphine oxide; and a coumarine-based compound such as 3,3'-carbonylvinyl-7-(diethylamino)coumarine, 3-(2-benzothiazolyl)-7-(diethylamino)coumarine, 3-benzoyl-7-(diethylamino)coumarine, 3-benzoyl-7-methoxy-coumarine, and 10,10'-carbonylbis[1,1,7,7-tetramethyl-2,3,6,7-tetrahydro-1H,5H,11H—Cl]-benzopyrano[6,7,8-ij]-quinolizine-11-one may be used alone or in a mixture of two or more.

In the photosensitive composition according to the exemplary embodiment of the present application, the content of the photopolymerization initiator may be 0.1 to 5 wt % based on the total weight of the photosensitive composition, but is not limited thereto.

The solvent, for example, may include one or more kinds selected from the group consisting of methyl ethyl ketone, methyl cellosolve, ethyl cellosolve, ethyleneglycol dimethyl ether, ethyleneglycol diethyl ether, propyleneglycol dimethyl ether, propyleneglycol diethyl ether, diethyleneglycol dimethylether, diethyleneglycol diethylether, diethyleneglycol methyl ethyl ether, 2-ethoxy propanol, 2-methoxy propanol, 3-methoxy butanol, cyclohexanone, cyclopentanone, propyleneglycol methyl ether acetate, propyleneglycol ethyl ether acetate, 3-methoxybutyl acetate, ethyl 3-ethoxypropionate, ethyl cellosolveacetate, methyl cellosolveacetate, butyl acetate, and dipropyleneglycol monomethyl ether, but is not necessarily limited thereto.

In the photosensitive composition according to the exemplary embodiment of the present application, the content of the solvent may be 45 to 95 wt % based on the total weight of the photosensitive composition, but is not limited thereto.

The photosensitive composition according to the exemplary embodiment of the present application may further include a colorant.

In the photosensitive composition according to the exemplary embodiment of the present application, one or more kinds of pigments or dyes or mixtures thereof may be used as the colorant. Specifically, metal oxides such as carbon black, graphite, and titanium black may be used as a black pigment. Examples of the carbon black include Cisto 5HIISAF-HS, Cisto KH, Cisto 3HHAF-HS, Cisto NH, Cisto 3M, Cisto 300HAF-LS, Cisto 116HMMAF-HS, Cisto 116MAF, Cisto FMFEF-HS, Cisto SOFEF, Cisto VGPF, Cisto SVHSRF-HS, and Cisto SSRF (Donghae Carbon, Co., Ltd.); Diagram black II, Diagram black N339, Diagram black SH, Diagram black H, Diagram LH, Diagram HA, Diagram SF, Diagram N550M, Diagram M, Diagram E, Diagram G, Diagram R, Diagram N760M, Diagram LR, #2700, #2600, #2400, #2350, #2300, #2200, #1000, #980, #900, MCF88, #52, #50, #47, #45, #45L, #25, #CF9, #95, #3030, #3050, MA7, MA77, MA8, MA11, MA100, MA40, OIL7B, OIL9B, OIL11B, OIL30B, and OIL31B (Mitsubishi Chemical, Co., Ltd.); PRINTEX-U, PRINTEX-V, PRINTEX-140U, PRINTEX-140V, PRINTEX-95, PRINTEX-85, PRINTEX-75, PRINTEX-55, PRINTEX-45, PRINTEX-300, PRINTEX-35, PRINTEX-25, PRINTEX-200, PRINTEX-40, PRINTEX-30, PRINTEX-3, PRINTEX-A, SPECIAL BLACK-550, SPECIAL BLACK-350, SPECIAL BLACK-250, SPECIAL BLACK-100, and LAMP BLACK-101 (Degussa, Co., Ltd.); RAVEN-1100ULTRA, RAVEN-1080ULTRA, RAVEN-1060ULTRA, RAVEN-1040, RAVEN-1035, RAVEN-1020, RAVEN-1000, RAVEN-890F, RAVEN-890, RAVEN-880ULTRA, RAVEN-860ULTRA, RAVEN-850, RAVEN-820, RAVEN-790ULTRA, RAVEN-780ULTRA, RAVEN-760ULTRA, RAVEN-520, RAVEN-500, RAVEN-460, RAVEN-450, RAVEN-430ULTRA, RAVEN-420, RAVEN-410, RAVEN-2500ULTRA, RAVEN-2000, RAVEN-1500, RAVEN-1255, RAVEN-1250, RAVEN-1200, RAVEN-1190ULTRA, and RAVEN-1170 (Columbia Carbon, Co., Ltd.), mixtures thereof or the like. Further, examples of the colorant exhibiting a color include carmine 6B (C.I. 12490), phthalocyanine green (C.I. 74260), phthalocyanine blue (C.I. 74160), perylene black (BASF K0084. K0086), cyanine black, linol yellow (C.I.21090), linol yellow GRO(C.I. 21090), benzidine yellow 4T-564D, victoria pure blue (C.I.42595), C.I. PIGMENT RED 3, 23, 97, 108, 122, 139, 140, 141, 142, 143, 144, 149, 166, 168, 175, 177, 180, 185, 189, 190, 192, 202, 214, 215, 220, 221, 224, 230, 235, 242, 254, 255, 260, 262, 264, and 272; C.I. PIGMENT GREEN 7, 36; C.I. PIGMENT blue 15:1, 15:3, 15:4, 15:6, 16, 22, 28, 36, 60, and 64; C.I. PIGMENT yellow 13, 14, 35, 53, 83, 93, 95, 110, 120, 138, 139, 150, 151, 154, 175, 180, 181, 185, 194, and 213; C.I. PIGMENT VIOLET 15, 19, 23, 29, 32, and 37, and the like, and in addition to this, a white pigment, a fluorescent pigment or the like may be used. A material in which zinc is used as the central metal other than copper may be used as the phthalocyanine-based complex compound used as the pigment.

In the photosensitive composition according to the exemplary embodiment of the present application, the content of the colorant may be 1 to 20 wt % based on the total weight of the photosensitive composition, but is not limited thereto.

The photosensitive composition according to the exemplary embodiment of the present application may further include one or two or more additives selected from the group consisting of a curing accelerator, a thermal polymerization inhibitor, a surfactant, a dispersing agent, an antioxidant, a UV absorbent, a leveling agent, a photosensitizer, a plasticizer, an adhesion promoter, a filler and an adhesion aid.

In the photosensitive composition according to the exemplary embodiment of the present application, the content of the additive may be 0.01 to 5 wt % based on the total weight of the photosensitive composition, but is not limited thereto.

In the photosensitive composition according to the exemplary embodiment of the present application, examples of the curing accelerator may include one or more kinds selected from the group consisting of 2-mercaptobenzoimidazole, 2-mercaptobenzothiazole, 2-mercaptobenzoxazole, 2,5-dimercapto-1,3,4-thiadiazole, 2-mercapto-4,6-dimethylaminopyrydine, pentaerythritol tetrakis(3-mercaptopropionate), pentaerythritol tris(3-mercaptopropionate), pentaerythritol tetrakis(2-mercaptoacetate), pentaerythritol tris(2-mercaptoacetate), trimethylolpropane tris(2-mercaptoacetate), trimethylolpropane tris(3-mercaptopropionate), trimethylolethane tris(2-mercaptoacetate), and trimethylolethane tris(3-mercaptopropionate), but are not limited thereto, and may include matters that are generally known in the art.

In the photosensitive composition according to the exemplary embodiment of the present application, examples of the thermal polymerization inhibitor may include one or more kinds selected from the group consisting of p-anisole, hydroquinone, pyrocatechol, t-butyl catechol, N-nitrosophenylhydroxyamine ammonium salts, N-nitrosophenylhydroxyamine aluminum salts and phenothiazine, but are not limited thereto and may include matters that are generally known in the art.

In the photosensitive composition according to the exemplary embodiment of the present application, examples of the surfactant may include MCF 350SF, F-475, F-488, F-552 (hereinafter, DIC, Co., Ltd.) and the like, but are not limited thereto.

In the photosensitive composition according to the exemplary embodiment of the present application, the dispersing agent may be used by a method of internally adding the dispersing agent to a pigment in a form of surface treatment of the pigment in advance or a method of externally adding the dispersing agent to the pigment.

In the photosensitive composition according to the exemplary embodiment of the present application, a polymer type, nonionic, anionic or cationic dispersing agent may be used as the dispersing agent. Non-limiting examples of the dispersing agent may include polyalkyleneglycol and esters thereof, polyoxyalkylene polyhydric alcohols, esteralkylene oxide additions, alcoholalkylene oxide additions, ester sulfonate, sulfonates, ester carboxylates, carboxylates, alkylamide alkylene oxide additions, alkylamine and the like, one kind or a mixture of two or more kinds selected from the examples may be used, but the examples are not limited thereto.

In the photosensitive composition according to the exemplary embodiment of the present application, non-limiting examples of the antioxidant may include one or more kinds selected from 2,2-thiobis(4-methyl-6-t-butylphenol) and 2,6-g,t-butylphenol, but are not limited thereto.

In the photosensitive composition according to the exemplary embodiment of the present application, non-limiting examples of the UV absorbent may include one or more kinds selected from 2-(3-t-butyl-5-methyl-2-hydroxyphenyl)-5-chloro-benzotriazol and alkoxy benzophenone, but are not limited thereto.

The exemplary embodiment of the present application provides a photosensitive material including the photosensitive composition.

The exemplary embodiment of the present application provides a photosensitive material manufactured by using the photosensitive composition.

The photosensitive composition is present in a state where at least a portion of the solvent is removed or photocured by drying and/or curing in the photosensitive material.

Meanwhile, the photosensitive composition according to the present application is used in a roll coater, a curtain coater, a spin coater, a slot die coater, and various printings and precipitations, and may be applied on a support of metal, paper, glass and plastic substrates. Further, after being applied on the support such as the film, the composition may be transferred on the other support, or the composition may be applied on a first support, transferred on a blanket, and transferred on a second support, and the application method thereof is not particularly limited.

Examples of a light source for curing the photosensitive composition according to the exemplary embodiment of the present application include a mercury vapor arc, a carbon arc, a Xe arc and the like emitting light having a wavelength of 250 to 450 nm, but are not necessarily limited thereto.

The photosensitive composition including the compound of the present application is preferably used in a pigment dispersion type photosensitive material for manufacturing a TFT LCD color filter, a photosensitive material for forming a black matrix of a TFT LCD or organic light emitting diode, a photosensitive material for forming an overcoat layer, and a column spacer photosensitive material, but may be used in manufacturing a photosensitive material for a photocurable paint, photocurable ink, photocurable adhesive, a printed board, and a printed circuit board, and other transparent photosensitive materials and PDPs, and the purpose thereof is not particularly limited.

Hereinafter, preferable Synthetic Examples, Examples and Comparative Examples will be described in order to help understand the present application. However, the following Synthetic Examples, Examples and Comparative Examples are set forth to illustrate the present application, but the scope of the present application is not limited thereto.

Synthetic Example 1

10 mol of 3-glycidoxypropyltrimethoxysilane (KBM-403 manufactured by Shinetsu, Co., Ltd.) was diluted in propylene glycol monomethyl ether acetate. The solution was maintained at 50° C., and the reaction was performed while 10 mol of N-methylallylamine (Aldrich) was slowly added. After the obtained solution was separated through the column, the solvent was removed by using the vacuum distillation to obtain the compound represented by the following Formula 5.

[Formula 5]

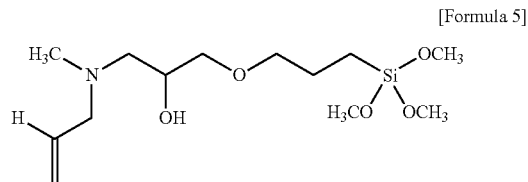

The structure was confirmed through $^1$H-NMR: 5.17, 5.15, 5.83 (—CH=CH$_2$), 2.27 (CH$_3$), 2.0 (—OH), 3.55 (—OCH$_3$)

Synthetic Example 2

Synthetic Example 2 was the same as Synthetic Example 1, except that 3-glycidoxypropyltriethoxysilane (KBE-403 manufactured by Shinetsu, Co., Ltd.) was used instead of 3-glycidoxypropyltrimethoxysilane (KBM-403 manufactured by Shinetsu, Co., Ltd.) in Synthetic Example 1. Thereby, the compound represented by the following Formula 6 was obtained.

[Formula 6]

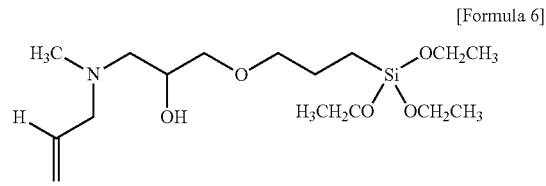

The structure was confirmed through $^1$H-NMR: 5.17, 5.15, 5.83 (—CH=CH$_2$), 2.27 (CH$_3$), 2.0 (—OH), 1.22, 3.83 (—OCH$_2$CH$_3$)

Synthetic Example 3

Synthetic Example 3 was the same as Synthetic Example 1, except that N-ethylallylamine (Aldrich) was used instead of N-methylallylamine (Aldrich) in Synthetic Example 1. Thereby, the compound represented by the following Formula 7 was obtained.

[Formula 7]

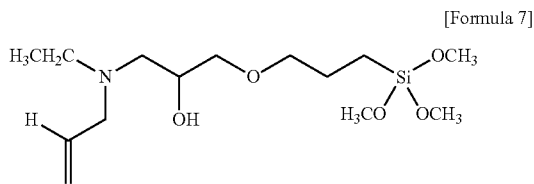

The structure was confirmed through $^1$H-NMR: 5.17, 5.15, 5.83 (—CH=CH$_2$), 2.40, 2.62 (—CH$_2$CH$_3$), 2.0 (—OH), 3.55 (—OCH$_3$)

Synthetic Example 4

Synthetic Example 4 was the same as Synthetic Example 3, except that 3-glycidoxypropyltriethoxysilane (KBE-403 manufactured by Shinetsu, Co., Ltd.) was used instead of 3-glycidoxypropyltrimethoxysilane (KBM-403 manufactured by Shinetsu, Co., Ltd.) in Synthetic Example 3. Thereby, the compound represented by the following Formula 8 was obtained.

[Formula 8]

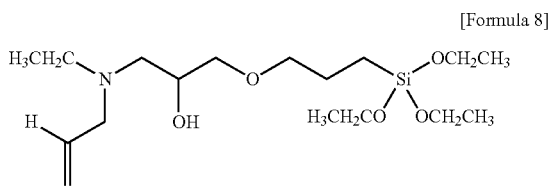

The structure was confirmed through $^1$H-NMR: 5.17, 5.15, 5.83 (—CH=CH$_2$), 2.40, 2.62 (—CH$_2$CH$_3$), 2.0 (—OH), 1.12, 3.83 (—OCH$_2$CH$_3$)

Synthetic Example 5

Synthetic Example 5 was the same as Synthetic Example 1, except that diallylamine (Aldrich) was used instead of N-methylallylamine (Aldrich) in Synthetic Example 1. Thereby, the compound represented by the following Formula 9 was obtained.

[Formula 9]

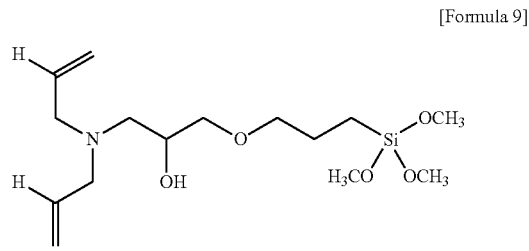 [SMILES: C=CCN(CC=C)CC(O)COCCC[Si](OC)(OC)OC]

The structure was confirmed through $^1$H-NMR: 5.17, 5.15, 5.83 (—CH=CH$_2$), 2.0 (—OH), 3.55 (—OCH$_3$)

Synthetic Example 6

Synthetic Example 6 was the same as Synthetic Example 5, except that 3-glycidoxypropyltriethoxysilane (KBE-403 manufactured by Shinetsu, Co., Ltd.) was used instead of 3-glycidoxypropyltrimethoxysilane (KBM-403 manufactured by Shinetsu, Co., Ltd.) in Synthetic Example 5. Thereby, the compound represented by Formula 10 was obtained.

[Formula 10]

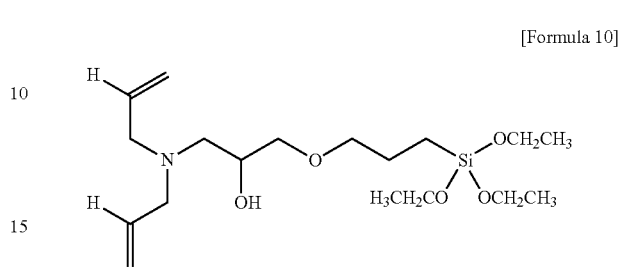

The structure was confirmed through $^1$H-NMR: 5.17, 5.15, 5.83 (—CH=CH$_2$), 2.0 (—OH), 1.22, 3.83 (—OCH$_2$CH$_3$)

Example 1

The following photosensitive compositions were manufactured in order to confirm the effect of the present application. 8 parts by weight of the binder BzMA/MAA (molar ratio: 70/30, Mw: 24,000) formed of the alkali soluble resin, 16 parts by weight of the dipentaerythritol hexaacrylate compound as the crosslinking compound, 1 part by weight of Irgacure 369 (2-benzyl-2-dimethylamino-1-(4-morpholinophenyl)-butane-1-one) manufactured by Ciba-Geigy, Co., Ltd. as the photopolymerization initiator, 0.01 parts by weight (0.05 wt % based on the solid) of the compound of Synthetic Example 1, and PGMEA that was the organic solvent were added so that the total content was 100 parts by weight, and mixed by using the shaker for 3 hours to obtain the solution by the filter of 5 microns.

After the uniform thin film was formed by applying the photosensitive composition by the method such as spin coating, slit coating, dip coating or doctor blading, the solvent was volatilized by performing the prebake process at 100° C. for 200 sec. The thickness of the dried thin film was about 2.5 microns.

The film was exposed under the high pressure mercury lamp by using an independent pattern type photomask where a diameter was constituted every 1 micron within 5 to 20 microns, developed by a spray method while the pattern was maintained in the KOH alkali aqueous solution having the pH of 11.3 to 11.7 at 30° C., washed with pure water, and dried by air blowing. After the state of the pattern was observed by the optical microscope, the size of the remaining minimum pattern was evaluated based on the diameter of the photomask.

Storage stability of the composition was measured as described below. First, after the viscosity of the initial composition was measured, the composition was contained in the sealed vessel and left in the oven maintained at 45° C. for 24 hours, and the viscosity thereof was measured again. The values obtained by dividing the degree of increase in viscosity by the initially measured viscosity were represented by % and compared.

Example 2

Example 2 was the same as Example 1, except that the compound of Synthetic Example 1 was used in the amount of 0.25 parts by weight (1 wt % based on the solid) instead of 0.01 parts by weight (0.05 wt % based on the solid) in Example 1.

Example 3

Example 3 was the same as Example 1, except that the compound of Synthetic Example 1 was used in the amount of 1.32 parts by weight (5 wt % based on the solid) instead of 0.01 parts by weight (0.05 wt % based on the solid) in Example 1.

Example 4

Example 4 was the same as Example 1, except that the compound of Synthetic Example 1 was used in the amount of 2.78 parts by weight (10 wt % based on the solid) instead of 0.01 parts by weight (0.05 wt % based on the solid) in Example 1.

Examples 5 to 8

Examples 5 to 8 were the same as Examples 1 to 4, respectively, except that the compound of Synthetic Example 2 was used instead of the compound of Synthetic Example 1 in Examples 1 to 4.

Examples 9 to 12

Examples 9 to 12 were the same as Examples 1 to 4, respectively, except that the compound of Synthetic Example 3 was used instead of the compound of Synthetic Example 1 in Examples 1 to 4.

Examples 13 to 16

Examples 13 to 16 were the same as Examples 1 to 4, respectively, except that the compound of Synthetic Example 4 was used instead of the compound of Synthetic Example 1 in Examples 1 to 4.

Examples 17 to 20

Examples 17 to 20 were the same as Examples 1 to 4, respectively, except that the compound of Synthetic Example 5 was used instead of the compound of Synthetic Example 1 in Examples 1 to 4.

Examples 21 to 24

Examples 21 to 24 were the same as Examples 1 to 4, respectively, except that the compound of Synthetic Example 6 was used instead of the compound of Synthetic Example 1 in Examples 1 to 4.

Comparative Examples 1 to 4

Comparative Examples 1 to 4 were the same as Examples 1 to 4, respectively, except that 3-glycidoxypropyltrimethoxysilane (KBM-403 manufactured by Shinetsu, Co., Ltd.) was used instead of the compound of Synthetic Example 1 in Examples 1 to 4.

Comparative Examples 5 to 8

Comparative Examples 5 to 8 were the same as Examples 1 to 4, respectively, except that 3-glycidoxypropyltriethoxysilane (KBE-403 manufactured by Shinetsu, Co., Ltd.) was used instead of the compound of Synthetic Example 1 in Examples 1 to 4.

Comparative Examples 9 to 12

Comparative Examples 9 to 12 were the same as Examples 1 to 4, respectively, except that 3-acryloxypropyltrimethoxysilane (KBM-5103 manufactured by Shinetsu, Co., Ltd.) was used instead of the compound of Synthetic Example 1 in Examples 1 to 4.

Comparative Examples 13 to 16

Comparative Examples 13 to 16 were the same as Examples 1 to 4, respectively, except that 3-methacryloxypropyltrimethoxysilane (KBM-503 manufactured by Shinetsu, Co., Ltd.) was used instead of the compound of Synthetic Example 1 in Examples 1 to 4.

Comparative Examples 17 to 20

Comparative Examples 17 to 20 were the same as Examples 1 to 4, respectively, except that vinyltrimethoxysilane (KBM-1003 manufactured by Shinetsu, Co., Ltd.) was used instead of the compound of Synthetic Example 1 in Examples 1 to 4.

Comparative Examples 21 to 24

Comparative Examples 21 to 24 were the same as Examples 1 to 4, respectively, except that 3-aminopropyltriethoxysilane (KBE-903 manufactured by Shinetsu, Co., Ltd.) was used instead of the compound of Synthetic Example 1 in Examples 1 to 4.

Comparative Example 25

Comparative Example 25 was the same as Example 1, except that nothing was used instead of the compound of Synthetic Example 1 in Example 1.

The experimental results of the Examples and the Comparative Examples are described in Table 1.

TABLE 1

| | Structure | | Content | | Experimental result | Storage stability |
| --- | --- | --- | --- | --- | --- | --- |
| | Synthetic Example | Formula | Based on the solid (wt %) | Based on the total content (wt %) | Minimum size of the remaining pattern (based on the mask) | Change amount in viscosity (%) |
| Example 1 | Synthetic Example 1 | Formula 5 | 0.05 | 0.01 | 12 | 0.1 |
| Example 2 | | | 1 | 0.25 | 8 | 0.3 |
| Example 3 | | | 5 | 1.32 | 8 | 1.2 |
| Example 4 | | | 10 | 2.78 | 8 | 4.5 |
| Example 5 | Synthetic Example 2 | Formula 6 | 0.05 | 0.01 | 11 | 0.2 |
| Example 6 | | | 1 | 0.25 | 9 | 0.5 |

TABLE 1-continued

|  | Structure | | Content | | Experimental result | Storage stability |
|---|---|---|---|---|---|---|
|  | Synthetic Example | Formula | Based on the solid (wt %) | Based on the total content (wt %) | Minimum size of the remaining pattern (based on the mask) | Change amount in viscosity (%) |
| Example 7 |  |  | 5 | 1.32 | 8 | 2.0 |
| Example 8 |  |  | 10 | 2.78 | 8 | 6.0 |
| Example 9 | Synthetic Example 3 | Formula 7 | 0.05 | 0.01 | 12 | 0.2 |
| Example 10 |  |  | 1 | 0.25 | 9 | 0.6 |
| Example 11 |  |  | 5 | 1.32 | 9 | 1.7 |
| Example 12 |  |  | 10 | 2.78 | 7 | 2.9 |
| Example 13 | Synthetic Example 4 | Formula 8 | 0.05 | 0.01 | 10 | 0.3 |
| Example 14 |  |  | 1 | 0.25 | 8 | 2.1 |
| Example 15 |  |  | 5 | 1.32 | 8 | 2.7 |
| Example 16 |  |  | 10 | 2.78 | 8 | 3.4 |
| Example 17 | Synthetic Example 5 | Formula 9 | 0.05 | 0.01 | 12 | 0.1 |
| Example 18 |  |  | 1 | 0.25 | 9 | 0.3 |
| Example 19 |  |  | 5 | 1.32 | 8 | 1.3 |
| Example 20 |  |  | 10 | 2.78 | 8 | 3.8 |
| Example 21 | Synthetic Example 6 | Formula 10 | 0.05 | 0.01 | 12 | 0.1 |
| Example 22 |  |  | 1 | 0.25 | 9 | 0.9 |
| Example 23 |  |  | 5 | 1.32 | 7 | 2.2 |
| Example 24 |  |  | 10 | 2.78 | 7 | 4.6 |
| Comparative Example 1 | 3-glycidoxypropyl-trimethoxysilane | | 0.05 | 0.01 | X | 0.1 |
| Comparative Example 2 |  |  | 1 | 0.25 | 19 | 1.1 |
| Comparative Example 3 |  |  | 5 | 1.32 | 19 | 1.7 |
| Comparative Example 4 |  |  | 10 | 2.78 | 17 | 2.6 |
| Comparative Example 5 | 3-glycidoxypropyl-triethoxysilane | | 0.05 | 0.01 | X | 0.2 |
| Comparative Example 6 |  |  | 1 | 0.25 | 18 | 0.9 |
| Comparative Example 7 |  |  | 5 | 1.32 | 18 | 1.6 |
| Comparative Example 8 |  |  | 10 | 2.78 | 17 | 2.2 |
| Comparative Example 9 | 3-acryloxypropyl-trimethoxysilane | | 0.05 | 0.01 | X | 0.3 |
| Comparative Example 10 |  |  | 1 | 0.25 | 19 | 0.6 |
| Comparative Example 11 |  |  | 5 | 1.32 | 18 | 0.9 |
| Comparative Example 12 |  |  | 10 | 2.78 | 16 | 1.1 |
| Comparative Example 13 | 3-methacryloxypropyl-trimethoxysilane | | 0.05 | 0.01 | X | 0.2 |
| Comparative Example 14 |  |  | 1 | 0.25 | 19 | 0.5 |
| Comparative Example 15 |  |  | 5 | 1.32 | 19 | 0.9 |
| Comparative Example 16 |  |  | 10 | 2.78 | 17 | 1.5 |
| Comparative Example 17 | Vinyltrimethoxysilane | | 0.05 | 0.01 | X | 0.6 |
| Comparative Example 18 |  |  | 1 | 0.25 | X | 0.9 |
| Comparative Example 19 |  |  | 5 | 1.32 | 20 | 2.5 |
| Comparative Example 20 |  |  | 10 | 2.78 | 18 | 4.1 |
| Comparative Example 21 | 3-aminopropyl-triethoxysilane | | 0.05 | 0.01 | X | 0.8 |
| Comparative Example 22 |  |  | 1 | 0.25 | X | 1.7 |
| Comparative Example 23 |  |  | 5 | 1.32 | X | 4.3 |
| Comparative Example 24 |  |  | 10 | 2.78 | 19 | 6.5 |
| Comparative Example 25 | — | | 0 | 0 | X | 0.1 |

As shown in the experimental results, it can be seen that if the compounds of Formulas 5 to 10 obtained from Synthetic Examples 1 to 6, which are a novel coupling agent of the present application, are used, attachment strength of the pattern is improved as compared to the case where 3-glycidoxypropyltrimethoxysilane or 3-glycidoxypropyltriethoxysilane that is a generally used known coupling agent is used, accordingly, even a smaller pattern remains. In the aforementioned Table, X means no pattern.

However, in the case where the use amount is more than 5 wt % based on the solid, the case where the change amount in viscosity is frequently more than 3% occurs, such that a possibility of affecting safety of products is increased. Therefore, in the case where the a novel coupling agent of the present application is used, it is preferable to apply the coupling agent in the amount of 0.05 to 5 wt % based on the solid.

What is claimed is:

1. A photosensitive composition comprising:
a coupling agent including one or more of compounds represented by the following Formula 1;
a binder resin including an alkali soluble polymer resin;
a crosslinking compound including two or more ethylenically unsaturated groups;
a photopolymerization initiator; and
a solvent:

[Formula 1]

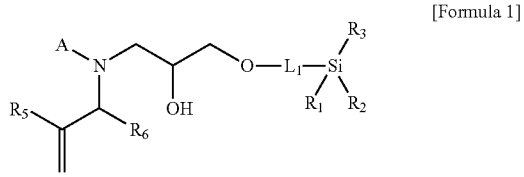

wherein
$L_1$ is a $C_3$-$C_8$ alkylene group which is unsubstituted or substituted by a $C_1$-$C_6$ alkyl group,
$R_1$ to $R_3$ are each independently a $C_1$-$C_3$ alkoxy group,
A is a $C_1$ to $C_3$ alkyl group or a $C_2$-$C_{14}$ alkenyl group,
$R_5$ is hydrogen or a $C_1$-$C_3$ alkyl group, and
$R_6$ is hydrogen or a $C_1$-$C_8$ alkyl group.

2. The photosensitive composition of claim 1, wherein Formula 1 is any one of the following Formula 2 to Formula 4:

[Formula 2]

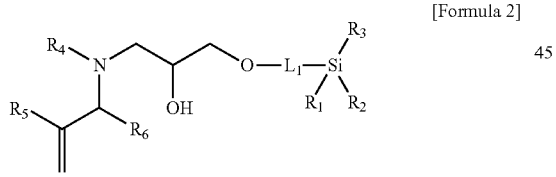

[Formula 3]

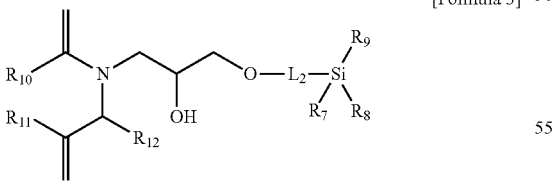

[Formula 4]

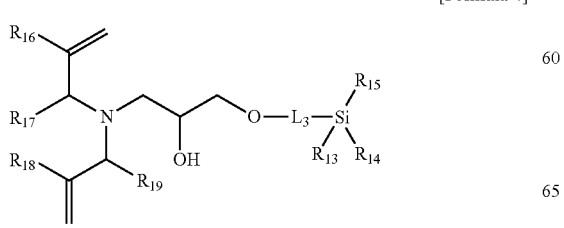

wherein
$L_1$ to $L_3$ are each independently a $C_3$-$C_8$ alkylene group which is unsubstituted or substituted by a $C_1$-$C_6$ alkyl group,
$R_1$ to $R_3$, $R_7$ to $R_9$ and $R_{13}$ to $R_{15}$ are each independently a $C_1$-$C_3$ alkoxy group,
$R_4$ is a $C_1$-$C_3$ alkyl group,
$R_5$, $R_{10}$, $R_{11}$, $R_{16}$ and $R_{18}$ are each independently hydrogen or a $C_1$-$C_3$ alkyl group, and
$R_6$, $R_{12}$, $R_{17}$ and $R_{19}$ are each independently hydrogen or a $C_1$-$C_8$ alkyl group.

3. The photosensitive composition of claim 2, wherein Formula 2 is any one selected from the group consisting of the following Formula 5 to Formula 8:

[Formula 5]

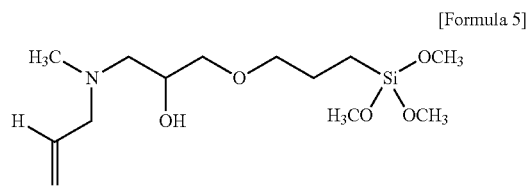

[Formula 6]

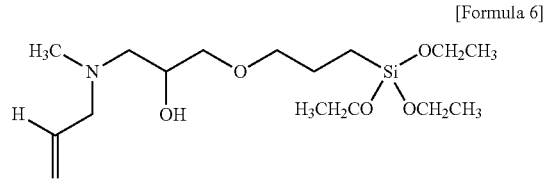

[Formula 7]

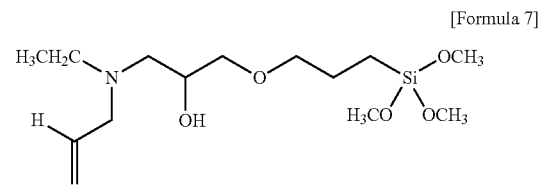

[Formula 8]

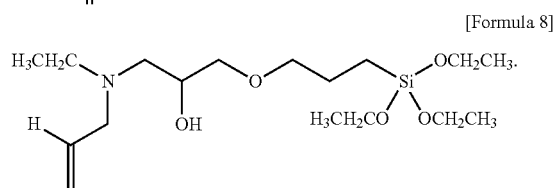

4. The photosensitive composition of claim 2, wherein Formula 4 is the following Formula 9 or Formula 10:

[Formula 9]

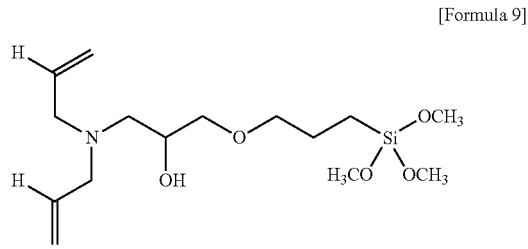

[Formula 10]

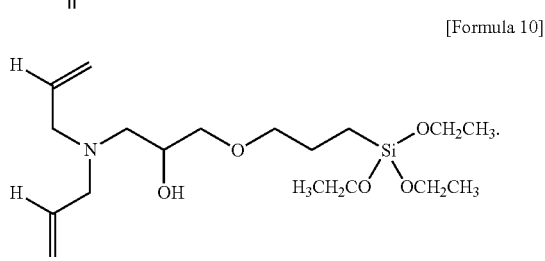

5. The photosensitive composition of claim 1, wherein a content of the coupling agent is 0.01 to 1.32 wt % based on a total weight of the photosensitive composition.

6. The photosensitive composition of claim 1, wherein a content of the coupling agent is 0.05 to 5 wt % based on a total weight of solid content of the photosensitive composition.

7. The photosensitive composition of claim 1, wherein a content of the binder resin is 1 to 20 wt % based on a total weight of the photosensitive composition.

8. The photosensitive composition of claim 1, wherein a content of the crosslinking compound is 1 to 30 wt % based on a total weight of the photosensitive composition.

9. The photosensitive composition of claim 1, wherein a content of the photopolymerization initiator is 0.1 to 5 wt % based on a total weight of the photosensitive composition.

10. The photosensitive composition of claim 1, wherein a content of the solvent is 45 to 95 wt % based on a total weight of the photosensitive composition.

11. The photosensitive composition of claim 1, further comprising: 1 to 20 wt % of a colorant based on a total weight of the photosensitive composition.

12. The photosensitive composition of claim 1, further comprising: 0.01 to 5 wt % of an additive based on a total weight of the photosensitive composition.

13. The photosensitive composition of claim 12, wherein the additive is one or two or more selected from the group consisting of a curing accelerator, a thermal polymerization inhibitor, a surfactant, a dispersing agent, an antioxidant, a UV absorbent, a leveling agent, a photosensitizer, a plasticizer, an adhesion promoter, a filler and an adhesion aid.

14. A photosensitive material manufactured by using the photosensitive composition of claim 1.

15. The photosensitive material of claim 14, wherein the photosensitive material is selected from the group consisting of a pigment dispersion type photosensitive material for manufacturing a TFT LCD color filter, a photosensitive material for forming a black matrix of a TFT LCD or an organic light emitting diode, a photosensitive material for forming an overcoat layer, a column spacer photosensitive material, and a photosensitive material for a printed circuit board.

16. A compound represented by the following Formula 2:

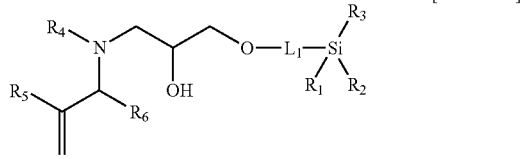

[Formula 2]

wherein
$L_1$ is a $C_3$-$C_8$ alkylene group which is unsubstituted or substituted by a $C_1$-$C_6$ alkyl group,
$R_1$ to $R_3$ are each independently a $C_1$-$C_3$ alkoxy group,
$R_4$ is a $C_1$-$C_3$ alkyl group,
$R_5$ is hydrogen or a $C_1$-$C_3$ alkyl group, and
$R_6$ is hydrogen or a $C_1$-$C_8$ alkyl group.

17. The compound of claim 16, wherein Formula 2 is any one selected from the group consisting of the following Formula 5 to Formula 8:

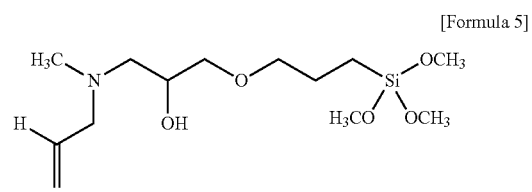

[Formula 5]

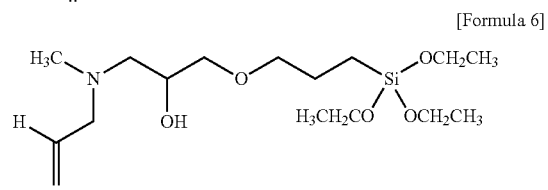

[Formula 6]

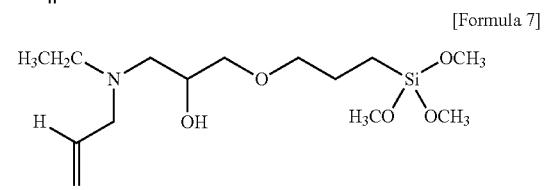

[Formula 7]

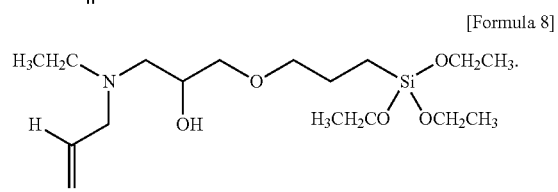

[Formula 8]

18. A compound represented by the following Formula 3:

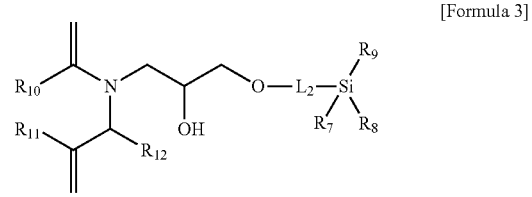

[Formula 3]

wherein
$L_2$ is hydrogen or a $C_3$-$C_8$ alkylene group which is unsubstituted or substituted by a $C_1$-$C_6$ alkyl group,
$R_7$ to $R_9$ are each independently a $C_1$-$C_3$ alkoxy group,
$R_{10}$ and $R_{11}$ are each independently hydrogen or a $C_1$-$C_3$ alkyl group, and
$R_{12}$ is hydrogen or a $C_1$-$C_8$ alkyl group.

* * * * *